United States Patent [19]
Hesse et al.

[11] Patent Number: 5,894,019
[45] Date of Patent: Apr. 13, 1999

[54] TOPICALLY APPLIED PHARMACEUTICAL COMPOSITION, METHOD OF PREPARING IT AND ITS USE

[75] Inventors: Ernst Hesse, Fieberbrunn; Gerhard Hantich, Kitzbühel; Volker Eisenreich, Fieberbrunn, all of Austria; Torsten Möller, Altenmarkt-Alz, Germany

[73] Assignee: GEBRO Broschek Gesellschaft m.b.H., Fieberbrunn, Austria

[21] Appl. No.: 08/913,409

[22] PCT Filed: Mar. 14, 1996

[86] PCT No.: PCT/AT96/00048

§ 371 Date: Sep. 17, 1997

§ 102(e) Date: Sep. 17, 1997

[87] PCT Pub. No.: WO96/29056

PCT Pub. Date: Sep. 26, 1996

[30] Foreign Application Priority Data

Mar. 17, 1995 [AT] Austria ..................... 475/95

[51] Int. Cl.$^6$ ............... A61K 9/14; A61K 6/00; A61K 7/00; A61K 9/127
[52] U.S. Cl. ............... 424/484; 424/401; 424/450; 424/487; 424/488; 514/825; 514/859; 514/863; 514/864; 514/887; 514/934; 514/938; 514/944
[58] Field of Search ................... 424/401, 484, 424/450, 487, 488; 514/938, 887, 944, 825, 859, 863, 864, 934

[56] References Cited

U.S. PATENT DOCUMENTS

| | | | |
|---|---|---|---|
| 4,897,269 | 1/1990 | Mezei | 424/450 |
| 5,064,655 | 11/1991 | Uster et al. | 424/450 |
| 5,549,901 | 8/1996 | Wright | 424/401 |

FOREIGN PATENT DOCUMENTS

| | | | |
|---|---|---|---|
| 0028110 | 5/1981 | European Pat. Off. | |
| 0376852 | 7/1990 | European Pat. Off. | |
| 2663538 | 6/1990 | France | |
| 0376852 | 7/1991 | France | A61K 9/16 |
| 3205504 | 8/1983 | Germany | |
| 3336047 | 4/1984 | Germany | |
| 4028906 | 3/1992 | Germany | |
| 62-223118 | 1/1987 | Japan | |
| 62-223119 | 1/1987 | Japan | |
| 2142534 | 1/1985 | United Kingdom | |
| 2236250 | 4/1991 | United Kingdom | |
| WO85/03640 | 8/1985 | WIPO | |
| WO91/04733 | 4/1991 | WIPO | |
| WO92/19225 | 11/1992 | WIPO | |
| WO93/15712 | 8/1993 | WIPO | |
| WO93/18752 | 9/1993 | WIPO | |
| WO94/00104 | 1/1994 | WIPO | |
| WO94/07460 | 4/1994 | WIPO | |
| WO94/17779 | 8/1994 | WIPO | |

*Primary Examiner*—José G. Dees
*Assistant Examiner*—Marina Lamm
*Attorney, Agent, or Firm*—Jacobson, Price, Holman & Stern, PLLC

[57] ABSTRACT

A topically applicable pharmaceutical composition comprises at least one liquid lipid, at least one pharmaceutical active ingredient which is soluble in at least one of the liquid lipids and is re-absorbed by the skin, and a hydrous gel which is the main component of the composition, whereby at least one lipid and at least one active ingredient are worked into the gel and the composition is essentially free of emulsifying agents and solid constituents, with the exception of the necessary gelatinizing agent required to form the hydrous gel. All of the active ingredients are present in dissolved form, whereby at least one active ingredient is dissolved in the liquid lipid, and this lipid containing the dissolved active ingredient is itself the internal phase and is worked into the hydrous gel as the external phase. The composition is also essentially free of surface-active substances.

Process for manufacturing a topically applicable pharmaceutical composition of this kind which provides for the fact that at least one active ingredient re-absorbable by the skin is dissolved, preferably in concentrated form, in a lipid and that this solution is intermingled as the internal phase in a hydrous gel as the external phase, whereby this hydrous gel is the main component in the composition.

The composition obtained thereby is highly stable and has favorable galenic properties.

39 Claims, No Drawings

TOPICALLY APPLIED PHARMACEUTICAL COMPOSITION, METHOD OF PREPARING IT AND ITS USE

This application is a 371 of PCT/AT96/00048 filed Mar. 14, 1996.

The invention refers to a topically applicable pharmaceutical composition which comprises:

At least one liquid lipid,
at least one pharmaceutical active ingredient which is soluble in at least one of the liquid lipids and is re-absorbed by the skin,
and a hydrous gel which is the main component of the composition, whereby at least one lipid and at least one active ingredient are worked into the gel and the composition is essentially free of emulsifying agents and solid constituents, with the exception of the necessary gelatinizing agent required to form the hydrous gel.

A hydrous gel is here defined as a dimensionally stable, semisolid hydrogel which is obtained by processing one or several gelatinizing agents (often referred to as thickening agents) with water.

A pharmaceutical composition of this kind is known (DE-A 3.336.047).

The conventional semisolid preparation forms of topically applicable pharmaceutical presentations consist essentially of hydrogels or lipogels, emulsions, ointments, and liposome preparations. These usual types of preparations generally have a wide variety of disadvantages, namely:

Hydrogels often have a drying effect on the skin, which is caused by the usually high content of highly volatile organic solvents they contain, especially various types of alcohol.

Emulsions have allergy potential due to the emulsifying agents contained within them and can therefore cause skin irritations.

Ointments and lipogels usually have a fatty base, which the skin can only absorb slowly and which can be bothersome because they often make the area surrounding the point of application (to clothing, etc.) greasy.

Liposome preparations are limited by the liposomes' relatively low degree of concentration.

On the other hand, it is desirable to apply numerous types of active ingredients topically. This is true, for example, of antirheumatic agents, local anesthetics, anti-allergic agents, substances to stimulate the circulation of blood, etc. For the above reasons, however, it has proven difficult to work the active ingredient into a carrier which possesses both favorable pharmaceutical and favorable cosmetic properties. Thus, for example, the release of the active ingredient from the pharmaceutical preparation must be guaranteed (in most cases, one also wants this release to take place as quickly as possible) as must the stability of the active ingredient and the dosage form itself. Other requirements are that the preparation be pleasant to apply, be absorbed quickly into the skin, and not cause skin irritations.

The difficulties outlined above are encountered to a high degree, for example, in the non-steroid antirheumatic agent ibuprofen since this active ingredient has a great tendency to recrystallize, even from within organic media. Thus, it was already proposed to work this active ingredient into a suitable matrix. It is known that benzyl alcohol (GB-A 2 236 250) or menthol (WO 91/04733), for example, can be used for this purpose. However, the dosage forms obtained thereby were still not completely satisfactory for the reasons cited above. The situation is similar for the topically applicable pharmaceutical composition mentioned at the start (DE-A 3 336 047) which also utilizes ibuprofen as an active ingredient, whereby the active ingredient is used in combination with a water-soluble, volatile low-molecular alkanol, water, a self-emulsifying lipid where appropriate, and a gel structuring agent.

There is therefore a need to create a topically applicable pharmaceutical composition of the kind mentioned at the start which avoids the disadvantages outlined above and which can be used universally so that, where required, an effective therapy is possible while avoiding a high blood level. In particular, it should be guaranteed that the pharmaceutical active ingredient is released easily from the dosage form upon its application so that it is quickly absorbed (resorbed) by the skin yet at the same time is kept stable within the dosage form and free from recrystallization. Other requirements are, as mentioned above, that the composition not dry out the skin and that skin irritations be avoided. The invention solves these tasks by having all the active ingredients contained in dissolved form, with at least one active ingredient being in the liquid lipid in dissolved form, and by having the lipid containing the dissolved active ingredient, as such as the internal phase, be intermingled in the hydrous gel as the external phase and by the composition being essentially free of surface-active substances. A composition of this kind can be referred to as a "dispersion gel". It is a two-phase system which has a lipid phase dispersed in a watery gel phase. There are one or several active ingredients dissolved in this lipid phase, which results in favorable penetration properties for the active ingredient. The advantage thereby is that much higher concentrations of active ingredient can be achieved at the site of action than is the case with conventional current presentations. The reason therefor is that—as compared with emulsions or ointments, for example—the composition in accordance with this invention makes do with proportionally much less fat. Assuming an equal concentration of active ingredient (with regard to the overall preparation), it is the case with the composition within the scope of this invention that, after the preparation is applied to the skin and the external watery phase evaporates, the active ingredient is present in a substantially higher concentration than with conventional two-phase systems and is available to a greater extent for resorption in accordance with the Fick's first principle of diffusion. Examples of lipid-soluble active ingredients which could be used are prednisolone, fluocortolone, triamcinolone, hydrocortisone, fusidic acid, clotrimazole, cyclopiroxolamine, tolnaftate, amphotericin B, dithranol, vitamin A, vitamin E, benzoyl peroxide, hexetidine, oestradiol, bufexamac, diclofenac, ketoprofen, piroxicam, indomethacin, flufenamic acid, felbinac, hydroxyethyl salicylate, etofenamat, naproxen, polidocanol, nicotinic acid benzyl ester, or ethylene glycol monosalicylate, but especially the non-steroid antirheumatic agent ibuprofen, particularly S(+)-ibuprofen, which can also be used in standard commercial pharmaceutical units, i.e. with just a small portion of R(-)ibuprofen. The latter active ingredient, but also other active ingredients usable in the pharmaceutical composition within the scope of this invention have the disadvantage of not being readily soluble and of having the tendency to recrystallize, even from within a large number of organic media. A surprising finding has now been made, namely that when these types of sensitive active ingredients, especially S(+)-ibuprofen, which has twice the analgesic and antiphlogistic effect of racemic ibuprofen, are combined with lipids, they form solutions of such stability in the state of being intermingled in the hydrogel phase that much larger droplet sizes of the internal phase (that is the phase containing the active ingredient) are tolerable without recrystallization occurring than is the case with conventional emulsions. The size of the dispersed droplets of the liquid lipid containing the active ingredient or the active ingredients is up to 60 µm, whereby the usual size of emulsion droplets in current preparations is in the nanometer range.

Moreover, the invention also makes it possible to easily introduce the active ingredient or the active ingredients in the lipid phase in highly concentrated form, preferably in supersaturated solution.

Owing to the fact that the pharmaceutical composition within the scope of this invention is essentially free of emulsifying agents, their disadvantageous effects (allergy potential) are sure to be avoided. Analogous statements can be made regarding the pharmaceutical composition being free of surface-active substances and free of solid constituents, because all active ingredients are present in soluble form and the lipid or the lipids is/are liquid. The hydrous gel constituting the external phase is only semisolid and contains no solid constituents with the exception of the solid thickening agents.

Owing to the fact that the lipid containing the dissolved active ingredient is worked into the hydrous gel as it is, i.e. that is without a change in the lipid's nature by formulating an emulsion by adding water (WO 93/18752), the work steps connected with changes in the lipid are eliminated as are the costs thereof.

In keeping with a preferred means of executing the invention, the pharmaceutical composition is also essentially free of volatile organic solvents and/or essentially free of volatile low-molecular alkanols and/or free of cosolvents which are mixable with water, e.g. propylene glycol, glycerol, or low-molecular liquid polyalcohols, polyethylene glycol.

In this context, the term "essentially" means that limited amounts of the afore-mentioned additives, e.g. alcohol, are tolerable as long as they do not impair the afore-mentioned major galenic advantages of the pharmaceutical composition within the scope of this invention. The absence of the afore-mentioned additive substance enables hypoallergenic preparations to be made and also enables the favorable properties mentioned at the start to have an optimum effect. Although no volatile organic solvents are used, no unpleasant feeling is created on the skin nor is the latter rendered excessively greasy. This is evidently due to the properties of the gel containing the portion of the afore-mentioned active ingredient in the lipid. A favorable aspect of the invention is the high water content in the preparation, which can be up to 90 percent by weight (in relation to the entire quantity). Despite this high water content, the composition within the scope of this invention has moisturizing properties, i.e. the gel is quickly absorbed by the skin and does not cause an unpleasant sensation for the patient. The pH value of the composition can be kept within the physiological range, i.e. between 5 and 6, without any problem.

Surprisingly, even though completely free of emulsifying agents and free of surface-active substances, the "dispersed" system, consisting of the lipid containing the active ingredient and the hydrogel, is stable in all regards.

For the liquid lipid phase, numerous natural and synthetic fats or oils are suitable for use within the scope of the invention, especially caster oil and/or almond oil and/or sesame oil and/or medium-chain triglycerides and/or mixtures of these substances.

To manufacture an alcohol-free gel, several known gelatinizing agents can be used, such as hydroxyethylcellulose and/or hydroxypropylcellulose and/or polymers of acrylic acid, which are known under the trade name "Carbopol" (registered trademark).

As mentioned above, it is favorable if the composition has a high water content, approx. up to 90 percent by weight. Despite the surplus of the non-solvent water, the active ingredient in the gel does not crystallize out.

With respect to the composition within the scope of the invention, in addition to the active ingredient dissolved in the lipid or the active ingredients dissolved therein, it is also possible to use at least one active ingredient that is not present in the gel in dissolved form but rather, for example, dissolved in the hydrous gel phase. Aside from the use of fat-soluble pharmaceutical preparations, this makes possible the additional use of water-soluble active ingredients in the external gel phase. With regard to these additional active ingredients, the properties of the dispersion gel are also utilized, namely that it does not irritate the skin, that it is moisturizing, quickly absorbed, and cosmetically pleasant. Examples of water-soluble active ingredients of this kind are gentamycin, neomycin, bacitracin, clindamycin, erythromycin, acyclovir, vidarabine, pantothenyl alcohol, allantoin, or hirudin. Of course, several pharmaceutical substances with varying solubility properties in the oily phase can be introduced and—as mentioned—also added in the watery phase.

The process in accordance with this invention which is used to make a topically applicable pharmaceutical composition in accordance with this invention of the type described above is characterized by the fact that at least one active ingredient resorbable by the skin is dissolved, preferably in concentrated form, in a lipid and that this solution is intermingled as the internal phase in a hydrous gel as the external phase, whereby the hydrous gel is the main component in the composition. In principle, these work procedures pose no difficulties and can be conducted with standard apparatus. For the sake of expediency, the dissolving process should be accompanied by heating, whereby the solution is cooled before being worked into the hydrous gel. Only moderate heating is required to promote the solution of the active ingredient or the active ingredients in the lipid or in the combination of lipids; it should not be too high so that thermal damage to the active ingredients, in particular, can be avoided.

The solution is worked into the gel by mixing until the desired degree of dispersion is achieved; for the sake of expediency, this should be done with conventional ointment kettles or ointment plants (e.g. such as those of the companies Fryma, Brogli, Suter). The degree of dispersion or the size of the fat or oil particles containing the active ingredient is determined largely by the selection of the dispersing tool. High-speed tools (homogenizers) yield particle sizes of up to 15 µm while simple mixers (e.g. blade mixers) yield droplet sizes of up to 60 µm.

The lipid particles containing the active ingredient and dispersed in the gel are usually spherical in shape and are therefore referred to hereinafter as "lipospheres".

A topically applicable pharmaceutical composition in accordance with this invention is particularly suitable for preparing dermatics or agents with an anti-inflammatory effect, especially anti-rheumatic agents; and is also suitable for preparing consolidants, hypoallergenic cosmetics, hypoallergenic dermatics, dermal vitamin preparations, therapeutic agents for treating acne, antimycotic agents, antibiotics, antipsoric agents, corticoid preparations, and antipruritics, further, in particular with ibuprofen, preferably S(+)-ibuprofen as an active ingredient to treat neurodermatitis.

The invention is described in detail below using examples by way of illustration:

EXAMPLE 1

150.0 g of S(+)-ibuprofen is dissolved in 300.0 g of castor oil with heat being added but no crystallization taking place. After cooling completely, the highly concentrated solution is worked into 2650 g of 1% polyacrylate gel (known under the trade name "Carbopol 940 NF") in a laboratory ointment mixer (Haagen & Rinau company) without the use of a homogenizer. The pH value of the gel obtained thereby is 5.5. The average particle size of the "lipospheres" is from 20 to 30 µm.

EXAMPLE 2

7.5 kg of S(+)-ibuprofen is dissolved in 15 kg of medium-chain triglycerides (known under the trade name "Miglyol 812") with heat being added but no crystallization taking place. After cooling completely, the highly concentrated solution is worked into 277.5 kg of 1% polyacrylate gel (known under the trade name "Carbopol 980 NF") in an ointment plant (Brogli company) utilizing a homogenizer. The pH value of the gel obtained thereby is 5.5. The average particle size of the "lipospheres" is from 5 to 10 µm.

EXAMPLE 3

20.0 g of phenyl salicylate is dissolved in 100.0 g of medium-chain triglycerides (known under the trade name "Tegosoft CT") and the solution obtained thereby is then worked into 880.0 g of 1% polyacrylate gel (known under the trade name "Carbopol 980") utilizing a homogenizer. The pH value of the gel obtained thereby is 5.9. The average particle size of the "lipospheres" is from 5 to 10 µm.

EXAMPLE 4

10.0 g of vitamin E acetate is dissolved in 100.0 g of neutral oil (known under the trade name "Miglyol 812") and the solution obtained thereby is then worked into 890.0 g of 1% polyacrylate gel (known under the trade name "Carbopol 980") utilizing a homogenizer. The pH value of the gel obtained thereby is 5.8. The average particle size of the "lipospheres" is from 5 to 15 µm.

EXAMPLE 5

23.0 g of nicotinic acid benzyl ester is dissolved in 117.0 g of almond oil and the solution obtained thereby is then worked into 860.0 g of 1% polyacrylate gel (known under the trade name "Carbopol 980") utilizing a homogenizer. The pH value of the gel obtained thereby is 5.85. The average particle size of the "lipospheres" is from 5 to 15 µm.

EXAMPLE 6

20.0 g of vitamin E acetate is dissolved in 100.0 g of avocado oil and the solution obtained thereby is then worked into 860.0 g of 1% polyacrylate gel (known under the trade name "Carbopol 980") utilizing a homogenizer. The pH value of the gel obtained thereby is 5.9. The average particle size of the "lipospheres" is from 5 to 15 µm.

EXAMPLE 7

5.0 g of hexetidine is dissolved in 115.0 g of medium-chain triglycerides (known under the trade name "Tegosoft CT"). 15.0 g of allantoin is added to 35.0 g of methylcellulose (known under the trade name "Methocel E 10 MC Premium") and 830.0 g of water and worked into a hydrous gel, whereby the allantoin is dissolved. Both phases are joined together utilizing a homogenizer. The pH value of the gel obtained thereby is 6.78. The average particle size of the "lipospheres" is from 15 to 20 µm.

EXAMPLE 8

5.0 g of S(+)-ibuprofen is dissolved in 10.0 g of caster oil with heat being added and no crystallization taking place. After cooling completely, the solution is worked by hand into 85.0 g of 5% hydroxyethylcellulose gel (known under the trade name "Tylose H 4000"). The pH value of the gel obtained thereby is 4.22. The average particle size of the "lipospheres" is 15 µm.

EXAMPLE 9

20.0 g of hydroxyethyl rutin is worked into 10.0 g of polyacrylate (known under the trade name "Carbopol 940") and the appropriate amount of sodium hydroxide to create 850.0 g of a hydrous gel with a pH value of 6.0, whereby the hydroxyethyl rutin is transferred dissolved in a gel. 50 g of S(+)-ibuprofen is then dissolved in 100.0 g of caster oil and the solution is brought into the gel phase by an homogenizer. The pH value of the gel obtained thereby is 5.6. The average particle size of the "lipospheres" is from 15 to 25 µm.

EXAMPLE 10

1.0 g of diclofenac sodium is dissolved in 10 g of caster oil, with a slight amount of heat being used in the process. After cooling completely, the solution is then worked into 89.0 g of 1% polyacrylate gel (known under the trade name "Carbopol 980"). The pH value of the gel obtained thereby is 5.6. The average particle size of the "lipospheres" is from 10 to 15 µm.

We claim:

1. A topically applicable pharmaceutical composition, comprising:
   at least one liquid lipid,
   at least one pharmaceutically active ingredient which is soluble in at least one of the liquid lipids and is resorbed by the skin,
   and a hydrous gel, whereby the at least one liquid lipid and the at least one active ingredient are worked into the gel and the composition is essentially free of emulsifying agents and solid constituents, with the exception of the necessary gelatinizing agent required to form the hydrous gel,
   wherein all the active ingredients are present in a dissolved form, with at least one active ingredient being in the liquid lipid in dissolved form, and the lipid containing the dissolved active ingredient is itself the internal phase, worked into the hydrous gel as the external phase, and the composition is essentially free of surface-active substances.

2. The composition according to claim 1, wherein it is essentially free of volatile organic solvents.

3. The composition according to claim 1, wherein it is essentially free of volatile low-molecular alkanols.

4. The composition according to claim 1, wherein it is essentially free of cosolvents which are mixable with water.

5. The composition according to claim 1, wherein the liquid lipid is selected from the group consisting of castor oil, almond oil, sesame oil, medium-chain triglycerides, and mixtures thereof.

6. The composition according to claim 1, wherein the gel contains hydroxyethylcellulose or hydroxypropylcellulose or polyacrylate or mixtures thereof.

7. The composition according to claim 1, wherein its water content can be up to 90 percent by weight of the total composition.

8. The composition according to claim 1, wherein at least one active ingredient is in the lipid in highly concentrated form.

9. The composition according to claim 1 wherein additionally, at least one active ingredient is present in the gel in a form other than being dissolved in the lipid.

10. The composition according to claim 1, wherein the at least one active ingredient is ibuprofen.

11. The composition according to claim 1, wherein at least one active ingredient is a non-steroid antirheumatic agent.

12. The composition according to claim 1, wherein at least one active ingredient is prednisolone, fluocortolone, triamcinolone, hydrocortisone, fusidic acid, clotrimazole, cyclopiroxolamine, tolnaftate, amphotericin B, dithranol, vitamin A, vitamin E, benzoyl peroxide, hexetidine, estradiol, bufexamac, polidocanol, nicotinic acid benzyl ester, or ethylene glycol monosalicylate.

13. The composition according to claim 9, wherein at least one active ingredient is gentamycin, neomycin, bacitracin, clindamycin, erythromycin, acyclovir, vidarabine, pantothenyl alcohol, allantoin, or hirudin.

14. A process for manufacturing a topically applicable pharmaceutical composition according to claim 1, wherein at least one active ingredient re-absorbable by the skin is dissolved in a lipid and the solution is intermingled as the internal phase in a hydrous gel as the external phase, whereby the hydrous gel is the main ingredient in the composition.

15. The process according to claim 14, wherein the dissolving process is accompanied by heating, whereby the solution is allowed to cool off before being worked into the hydrous gel.

16. The process according to claim 14, wherein the procedure of dissolving the active ingredient in the lipid is continued until a supersaturated solution is obtained.

17. The process according to claim 14, wherein the solution is worked into the gel by mixing until the desired degree of dispersion is achieved.

18. The composition according to claim 4, wherein the composition is essentially free of co-solvents selected from the group consisting of propylene glycol, glycerol, and low-molecular liquid polyalcohols.

19. The composition according to claim 18, wherein the low-molecular liquid polyalcohol is polyethylene glycol.

20. The composition according to claim 8, wherein the active ingredient is in supersaturated solution.

21. The composition according to claim 10, wherein the ibuprofen is S(+) ibuprofen.

22. The composition according to claim 11, wherein the non-steroidal anti-rheumatic agent is selected from the group consisting of diclofenae, ketoprofen, piroxicam, indomethacin, flufenamic acid, felbinac, hydroxyethyl salicylate, etofenamat and naproxen.

23. The process according to claim 14, wherein the active ingredient is dissolved in a concentrated form.

24. The composition according to claim 1 in the form of a dermatic preparation.

25. The composition according to claim 24, wherein the dermatic preparation is hypoallergenic.

26. The composition according to claim 24, wherein the dermatic preparation has an antibiotic effect.

27. The composition according to claim 1 in the form of an anti-rheumatic agent.

28. The composition according to claim 27, wherein the anti-rheumatic agent has an anti-inflammatory effect.

29. The composition according to claim 1, in the form of a consolidant preparation.

30. The composition according to claim 1 in the form of an anti-hemorrhoidal preparation.

31. The composition according to claim 1 in the form of an anti-psoric agent.

32. The composition according to claim 1 in the form of an anti-mycotic agent.

33. The composition according to claim 1 in the form of a dermal glucocorticoid preparation.

34. The composition according to claim 1 in the form of a dermal vitamin preparation.

35. A method for the treatment of herpes simplex comprising administering an effective amount of a composition according to claim 1 to a patient in need thereof.

36. A method for the treatment of acne comprising administering an effective amount of a composition according to claim 1 to a patient in need thereof.

37. A method for the treatment of neurodermatitis comprising administering an effective amount of a composition according to claim 1 to a patient in need thereof.

38. The composition according to claim 1, wherein additionally, at least one active ingredient is present in the gel in a form other than being dissolved in the watery gel phase.

39. The composition according to claim 1, wherein the hydrous gel is the main component of the composition.

* * * * *